United States Patent
Clinger et al.

(10) Patent No.: US 12,310,867 B2
(45) Date of Patent: *May 27, 2025

(54) STENT WITH LONGITUDINAL VARIABLE WIDTH STRUTS

(71) Applicant: DePuy Synthes Products, Inc., Raynham, MA (US)

(72) Inventors: Melissa Clinger, Raynham, MA (US); Peter Forsythe, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1055 days.

This patent is subject to a terminal disclaimer.

(21) Appl. No.: 17/170,299

(22) Filed: Feb. 8, 2021

(65) Prior Publication Data

US 2021/0161689 A1    Jun. 3, 2021

Related U.S. Application Data

(63) Continuation of application No. 16/116,612, filed on Aug. 29, 2018, now Pat. No. 10,932,927.

(51) Int. Cl.
*A61F 2/24* (2006.01)
*A61F 2/88* (2006.01)
(Continued)

(52) U.S. Cl.
CPC ............ *A61F 2/90* (2013.01); *A61F 2/88* (2013.01); *A61F 2/92* (2013.01);
(Continued)

(58) Field of Classification Search
CPC .... A61F 2/88; A61F 2/90; A61F 2/915; A61F 2/92; A61F 2002/91558;
(Continued)

(56) References Cited

U.S. PATENT DOCUMENTS 5,449,373 A * 9/1995 Pinchasik ............... A61F 2/915
                                                  606/198
5,554,180 A * 9/1996 Turk ....................... A61F 2/82
                                                  606/198
(Continued)

OTHER PUBLICATIONS

"Codman Neuro Announces Launch of Codman Enterprise 2," published Feb. 18, 2016, available at https://www.depuysynthes.com/about/news-press/qs/codman-neuro-announces-launch-of-codman-enterprise-2- as of this filing.

(Continued)

*Primary Examiner* — Seema Mathew
(74) *Attorney, Agent, or Firm* — Troutman Pepper Locke LLP

(57) ABSTRACT

Stents generally can include multiple longitudinal elements each extending over a majority of the length of the stent and each having alternating flexible and rigid segments. The stents can include nodes positioned between the flexible and rigid segments on the longitudinal elements and interconnecting members extending circumferentially to connect adjacent longitudinal elements at the nodes. The longitudinal elements can have a wave pattern and the interconnecting members can have a branch structure connecting peaks from one longitudinal element to troughs of an adjacent longitudinal element. The resulting stent structure can have lateral and longitudinal flexibility needed to navigate and conform to intracranial arteries with the benefits of recapturability and structural integrity of a closed cell design.

17 Claims, 7 Drawing Sheets

(51) Int. Cl.
*A61F 2/90* (2013.01)
*A61F 2/92* (2013.01)
*A61B 17/00* (2006.01)
*A61B 17/12* (2006.01)
*A61F 2/915* (2013.01)
*A61F 2/95* (2013.01)
*A61L 31/02* (2006.01)

(52) U.S. Cl.
CPC ............. *A61B 2017/00867* (2013.01); *A61B 17/12113* (2013.01); *A61F 2002/91575* (2013.01); *A61F 2/95* (2013.01); *A61L 31/022* (2013.01)

(58) Field of Classification Search
CPC .. A61F 2002/91566; A61F 2002/91575; A61F 2002/91583; A61F 2250/0029; A61F 2250/0036; A61F 2/91; A61F 2002/9155
See application file for complete search history.

(56) References Cited

U.S. PATENT DOCUMENTS

| | | | | |
|---|---|---|---|---|
| 5,601,593 A * | 2/1997 | Freitag | ............... | A61F 2/90 606/198 |
| 5,776,183 A * | 7/1998 | Kanesaka | ............... | A61F 2/91 606/198 |
| 5,807,404 A * | 9/1998 | Richter | ............... | A61F 2/915 623/1.16 |
| 5,824,059 A * | 10/1998 | Wijay | ............... | A61F 2/91 623/1.15 |
| 5,827,321 A * | 10/1998 | Roubin | ............... | A61F 2/91 606/198 |
| 5,855,600 A * | 1/1999 | Alt | ............... | A61F 2/915 606/195 |
| 5,911,754 A * | 6/1999 | Kanesaka | ............... | A61F 2/91 606/198 |
| 5,938,682 A * | 8/1999 | Hojeibane | ............... | A61F 2/915 606/198 |
| 6,048,361 A * | 4/2000 | Von Oepen | ............... | A61F 2/915 606/198 |
| 6,071,308 A * | 6/2000 | Ballou | ............... | A61F 2/90 606/198 |
| 6,099,561 A * | 8/2000 | Alt | ............... | A61F 2/915 623/1.34 |
| 6,113,627 A * | 9/2000 | Jang | ............... | A61F 2/915 623/1.49 |
| 6,129,755 A * | 10/2000 | Mathis | ............... | A61F 2/91 623/1.15 |
| 6,190,406 B1 * | 2/2001 | Duerig | ............... | A61F 2/915 623/1.2 |
| 6,270,524 B1 * | 8/2001 | Kim | ............... | A61F 2/89 623/1.11 |
| 6,312,459 B1 | 11/2001 | Huang et al. | | |
| 6,325,825 B1 * | 12/2001 | Kula | ............... | A61F 2/915 623/1.3 |
| 6,605,110 B2 | 8/2003 | Harrison | | |
| 6,635,083 B1 * | 10/2003 | Cheng | ............... | A61F 2/91 623/1.15 |
| 6,673,106 B2 | 1/2004 | Mitelberg et al. | | |
| 6,706,061 B1 * | 3/2004 | Fischell | ............... | A61F 2/915 623/1.15 |
| 6,852,124 B2 | 2/2005 | Cox et al. | | |
| 6,962,603 B1 | 11/2005 | Brown et al. | | |
| 6,997,946 B2 | 2/2006 | Girton et al. | | |
| 7,081,130 B2 * | 7/2006 | Jang | ............... | A61F 2/91 623/1.31 |
| 7,534,258 B2 | 5/2009 | Gomez et al. | | |
| 7,867,272 B2 * | 1/2011 | Niermann | ............... | A61F 2/915 623/1.15 |
| 8,500,793 B2 * | 8/2013 | Zipse | ............... | A61F 2/966 623/1.2 |
| 9,155,644 B2 | 10/2015 | Schroeder | | |
| 9,168,161 B2 | 10/2015 | Donovan et al. | | |
| 9,795,496 B2 | 10/2017 | Armstrong et al. | | |
| 2001/0047201 A1 * | 11/2001 | Cox | ............... | A61F 2/91 623/1.16 |
| 2002/0007209 A1 * | 1/2002 | Scheerder | ............... | A61L 31/088 219/121.72 |
| 2002/0062149 A1 * | 5/2002 | Jang | ............... | A61F 2/915 606/198 |
| 2002/0107562 A1 * | 8/2002 | Hart | ............... | E21B 23/06 623/1.15 |
| 2002/0121497 A1 * | 9/2002 | Tomonto | ............... | A61F 2/91 216/75 |
| 2002/0123797 A1 * | 9/2002 | Majercak | ............... | A61F 2/915 623/1.16 |
| 2003/0014101 A1 * | 1/2003 | Harrison | ............... | A61F 2/91 623/1.15 |
| 2003/0069630 A1 * | 4/2003 | Burgermeister | ............... | A61F 2/91 623/1.34 |
| 2004/0006382 A1 * | 1/2004 | Sohier | ............... | A61F 2/91 623/1.42 |
| 2004/0102833 A1 * | 5/2004 | Girton | ............... | A61F 2/915 623/1.11 |
| 2004/0117002 A1 * | 6/2004 | Girton | ............... | A61F 2/91 623/1.15 |
| 2004/0243216 A1 * | 12/2004 | Gregorich | ............... | A61F 2/915 623/1.15 |
| 2006/0030928 A1 * | 2/2006 | Burgermeister | ............... | A61L 31/14 623/1.15 |
| 2006/0030930 A1 * | 2/2006 | Burgermeister | ............... | A61F 2/91 623/1.15 |
| 2006/0136042 A1 * | 6/2006 | Holman | ............... | A61F 2/91 623/1.42 |
| 2006/0200227 A1 * | 9/2006 | Jang | ............... | A61F 2/915 623/1.15 |
| 2006/0217795 A1 * | 9/2006 | Besselink | ............... | A61B 17/11 623/1.15 |
| 2008/0086190 A1 * | 4/2008 | Ta | ............... | A61F 2/89 623/1.11 |
| 2008/0132995 A1 * | 6/2008 | Burgermeister | ............... | A61L 31/18 623/1.42 |
| 2009/0112306 A1 * | 4/2009 | Bonsignore | ............... | A61F 2/915 623/1.49 |
| 2009/0163989 A1 * | 6/2009 | Contiliano | ............... | A61F 2/915 623/1.15 |
| 2009/0192590 A1 | 7/2009 | Penn et al. | | |
| 2009/0228088 A1 * | 9/2009 | Lowe | ............... | A61F 2/91 623/1.2 |
| 2010/0004728 A1 * | 1/2010 | Rao | ............... | A61F 2/91 623/1.11 |
| 2010/0094391 A1 * | 4/2010 | Heraty | ............... | A61F 2/91 623/1.11 |
| 2010/0100166 A1 * | 4/2010 | Richter | ............... | A61F 2/915 623/1.2 |
| 2010/0298921 A1 * | 11/2010 | Schlun | ............... | A61F 2/91 623/1.2 |
| 2010/0324659 A1 * | 12/2010 | Mews | ............... | A61F 2/915 623/1.16 |
| 2011/0066225 A1 * | 3/2011 | Trollsas | ............... | A61L 31/148 623/1.46 |
| 2011/0106237 A1 * | 5/2011 | Bonsignore | ............... | A61F 2/915 623/1.15 |
| 2015/0209165 A1 | 7/2015 | Grandfield et al. | | |
| 2016/0015402 A1 | 1/2016 | Brady et al. | | |

OTHER PUBLICATIONS

Extended European Search Report issued in corresponding European Patent Application No. 19 19 4174 dated May 26, 2020.

* cited by examiner

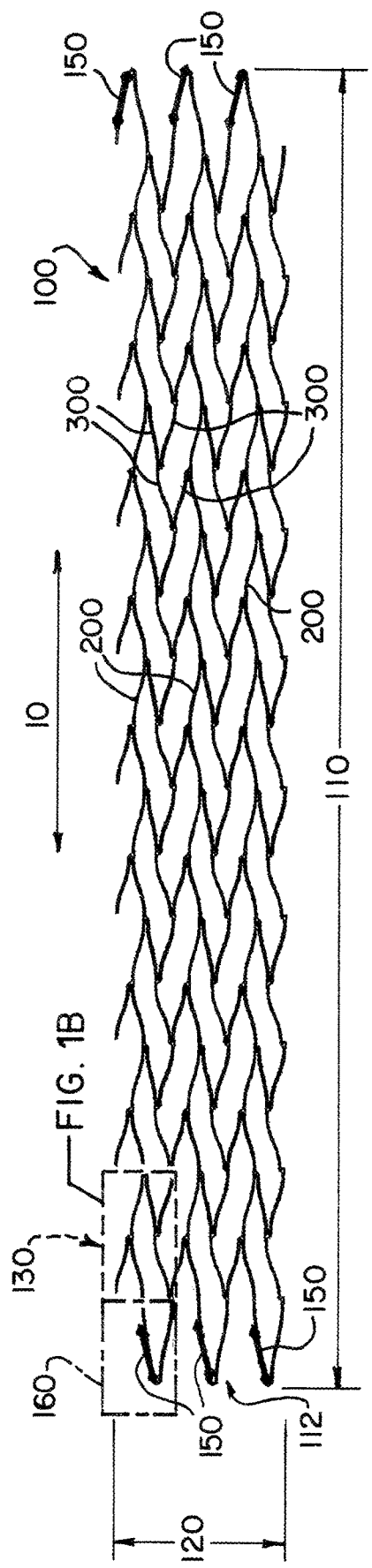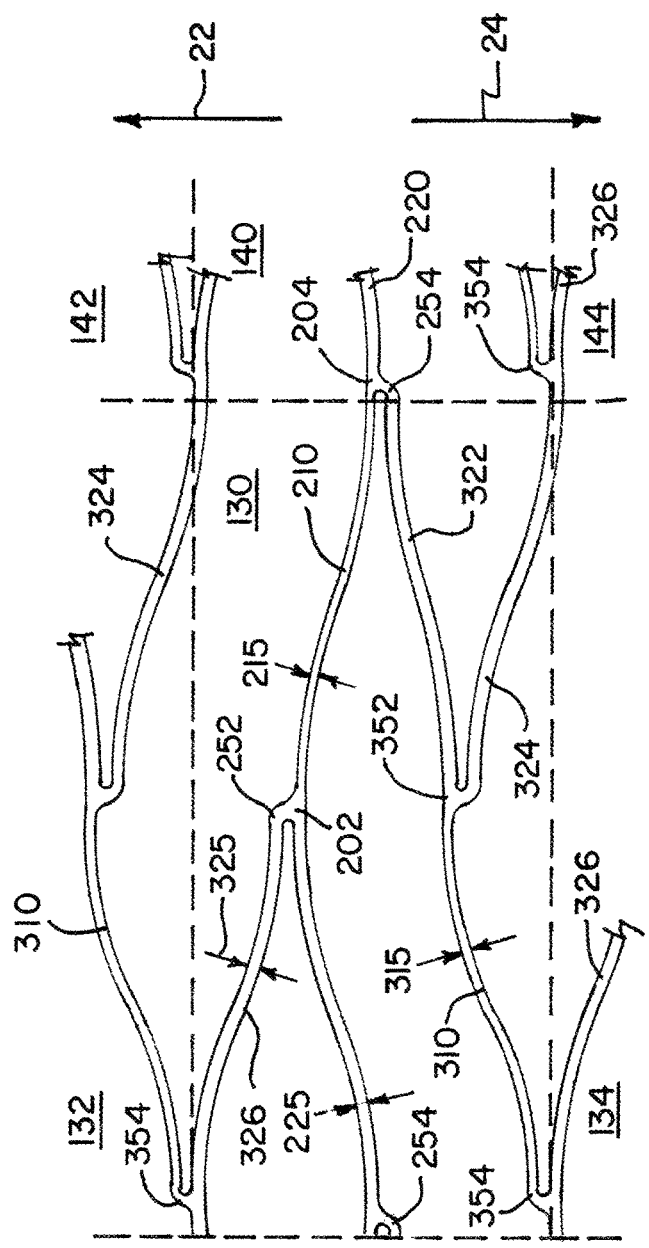

STENT WITH LONGITUDINAL VARIABLE WIDTH STRUTS

CROSS-REFERENCE TO RELATED APPLICATIONS

This application is a Continuation of U.S. application Ser. No. 16/116,612 filed on Aug. 29, 2018 which is incorporated herein by reference in its entirety herein into this application as if set forth in full.

FIELD OF INVENTION

The present invention generally relates to implantable stent medical devices, methods for manufacturing the same, and more particularly, to stents for treating wide-necked intracranial aneurysms.

BACKGROUND

Medical stents are used for supporting, maintaining, or repairing a lumen, passageway or opening in a living body. Stent design is unique to location and objective of the treatment as the stent must be flexible enough to navigate body lumen to arrive at a treatment site and then structurally robust enough to provide the required structural support to repair the treatment site. Compared with carotid arteries, the arteries inside the brain are very small and make many twists and turns, requiring a more flexible stent capable of not only navigating tight turns upon approaching a treatment site, but conforming to vessel walls within tight curvatures when implanted. Stents implanted to support embolic coil masses in cranial aneurysms must also be strong enough to maintain complete aneurysm neck coverage and serve as a scaffold or barrier to prevent the coils from protruding back into the parent blood vessel, particularly in the treatment of wide-necked aneurysms.

To meet the competing needs of flexibility and structural integrity, known stent designs typically include a plurality of circumferential rings or single helical coil designed to provide structural support joined by longitudinally extending bridges designed to achieve desired flexibility. A stent with a bridge at every joint is typically classified as a closed cell stent, and stent with many bridges removed is typically classified as an open cell stent. In general, open cell stents are more flexible than closed cell stents, making them easier to navigate tight curves when being delivered to a treatment site, or for increased conformability when treating a treatment site that includes a curve. However, the increased flexibility comes at the cost of loss of structural benefits such as scaffolding uniformity. Additionally, once deployed, open cell structures can be more difficult to recapture and reposition compared to closed cell stents. Closed cell designs typically have structural benefits such as scaffolding uniformity but at the cost of the flexibility and conformity required for intracranial treatments.

Known stents include the Cordis Enterprise® line of self-expanding stents, which are described in numerous patents and published patent applications including U.S. Pat. No. 6,673,106 which is hereby incorporated by reference hereinto.

There is therefore a need for an improved flexible neurovasculature stent capable of navigating tight curves to reach a treatment site, and once implanted conform to tight curvatures of vessel walls and maintain structural support for embolic implants.

SUMMARY

Disclosed herein are various exemplary stents of the present invention that can address the above needs, the stents generally can include multiple longitudinal elements each extending over a majority of the length of the stent and each having alternated flexible and rigid segments. The stents can include nodes positioned between the flexible and rigid segments on the longitudinal elements and interconnecting members extending circumferentially to connect adjacent longitudinal elements at the nodes. The longitudinal elements can have a wave pattern and the interconnecting members can have a branch structure connecting peaks from one longitudinal element to troughs of an adjacent longitudinal element. The resulting stent structure can have lateral and longitudinal flexibility needed to navigate and conform to intracranial arteries with the benefits of recapturability and structural integrity of a closed cell design.

In one example, a stent can be substantially tubular with a circumference and a length extending between a first open end and a second open end. The stent can have multiple longitudinal elements each having alternated thin and thick segments, and each longitudinal element can extend over a majority of the length of the stent. The stent can have interconnecting members that extend circumferentially to connect two adjacent longitudinal elements. The interconnecting members can have a plurality of branches. The stent can have a plurality of nodes positioned on the longitudinal elements between the alternating thin and thick segments. The nodes can connect the branches of the interconnecting members to the longitudinal elements. The thin segments and thick segments can respectively have uniform widths spanning between nodes such that the thick segments have a width that measures greater than the thin segments.

Each longitudinal element can have a sinusoidal shape. Each of the nodes can be positioned at a peak or a trough of the sinusoidal shape.

The interconnecting members can have thin branches and thick branches respectively having uniform widths such that the width of the thick branches measures greater than the thin branches. The interconnecting members can have four branches joined at two intermediate nodes. Of the four branches, a first branch can have a thin width and a second branch can have a thick width measuring greater than the thin width.

In another example a stent can have a substantially tubular shape with unit cells repeating in a clockwise direction, counterclockwise direction, and longitudinal direction. Each of the unit cells can have a longitudinally extending element extending the width of the unit cell in the longitudinal direction and forming one period of a wave pattern. The longitudinally extending element of the unit cell can have a clockwise note positioned at a trough of the wave pattern, a clockwise node positioned at a peak of the wave pattern, a thick segment of substantially uniform width extending from the counterclockwise node to the clockwise node, and a thin segment comprising a substantially uniform width measuring less than the width of the thick segment extending from the clockwise node to a longitudinally adjacent counterclockwise node of a longitudinally adjacent unit cell. The unit cell can have a clockwise extending branch extending from the clockwise node of the longitudinal element circumferentially in the clockwise direction. The unit cell can have a counterclockwise extending branch extending from the counterclockwise node of the longitudinal element in the counterclockwise direction.

The unit cell can have a first intermediate branch connecting a longitudinally adjacent counterclockwise extending branch extending from the longitudinally adjacent unit cell and a counterclockwise adjacent clockwise extending branch extending from a counterclockwise adjacent unit cell. The unit cell can have a second intermediate branch connecting the longitudinally adjacent counterclockwise extending branch and a diagonally adjacent clockwise extending branch extending from a unit cell counterclockwise adjacent the longitudinally adjacent unit cell.

The clockwise extending branch and the counterclockwise extending branch of the unit cell can each have a substantially uniform width that is about equal for both branches, and the first intermediate branch can have a substantially uniform width that measures less than the width of the clockwise extending branch and the counterclockwise extending branch.

The wave pattern of the longitudinal element can be in the shape of a sinusoid.

The width of the thick segment in the unit cell can measure about 0.0018 inches, and the width of the thin segment can measure about 0.00125 inches.

The stent can have a first end, a second end, a length extending longitudinally between the first and second ends with unit cells repeating over a majority of the length, and end cells positioned approximate the first and second ends. Each end cell can have an end segment of the longitudinally extending element, an end branch of the interconnecting member, and a joining member connecting the end segment to the end branch. The end cells can repeat in the clockwise and counterclockwise directions around the circumference of the stent at the stent ends.

In another example, a stent can have a substantially tubular shape characterized by a circumference measured in a circumferential direction and a length measured in a longitudinal direction. The stent can have longitudinal elements extending over the length of the stent made up of alternating flexible segments and rigid segments such that the flexible segments and rigid segments provide structural support for the stent and the flexible segments are more flexible in the longitudinal direction compared to the rigid segments. The stent can have interconnecting members that each connect two adjacent longitudinal elements in the circumferential direction. The interconnecting members can each have multiple branches. The stent can have nodes positioned on the longitudinal elements between each of the alternating flexible and rigid segments. The nodes can connect the branches of the interconnecting members to the longitudinal elements.

The flexible segments can have a thin width and the rigid segments can have a thick width that is greater than the thin width.

The interconnecting members can each have a flexible branch and a rigid branch such that the flexible branch has a greater flexibility in the longitudinal direction compared to the rigid branch.

The longitudinal elements of the stent can have a wave shape characterized by peaks and troughs. Each node of the stent can be positioned at a peak or a trough, and each interconnecting member can connect peaks from a first longitudinal element to troughs from a second longitudinal element.

In an example method for manufacturing a stent, an elastic tubing with a circumferential direction and a longitudinal direction can be provided. The tubing can be cut to form a first alternating pattern of flexible struts and rigid struts extending in the longitudinal direction. Each of the flexible struts can be more flexible than each of the rigid struts as measured in the longitudinal direction. First nodes can be positioned at each intersection of the flexible struts and rigid struts of the first alternating pattern. The tubing can be cut to form first branches each extending from each of the first nodes. The tubing can be cut to form at least one adjacent alternating pattern of flexible struts and rigid struts extending in the longitudinal direction and positioned adjacent to the first alternating pattern in the circumferential direction. The first branches can be connected to each adjacent alternating pattern.

Each of the flexible struts can be cut to a substantially uniform thin width between a first pair of adjacent nodes, and each of the rigid struts can be cut to a substantially uniform thick width between a second pair of adjacent nodes such that each of the flexible struts has a width that measures less than each of the width of each of the rigid struts.

Intermediate branches can be cut to extend from the first branches, and the intermediate branches can each have a width less than a width of the first branch from which it extends.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1A illustrates a strut pattern of an unrolled stent according to aspects of the present invention.

FIG. 1B illustrates a unit cell according to aspects of the present invention.

DETAILED DESCRIPTION

Figure 1C:
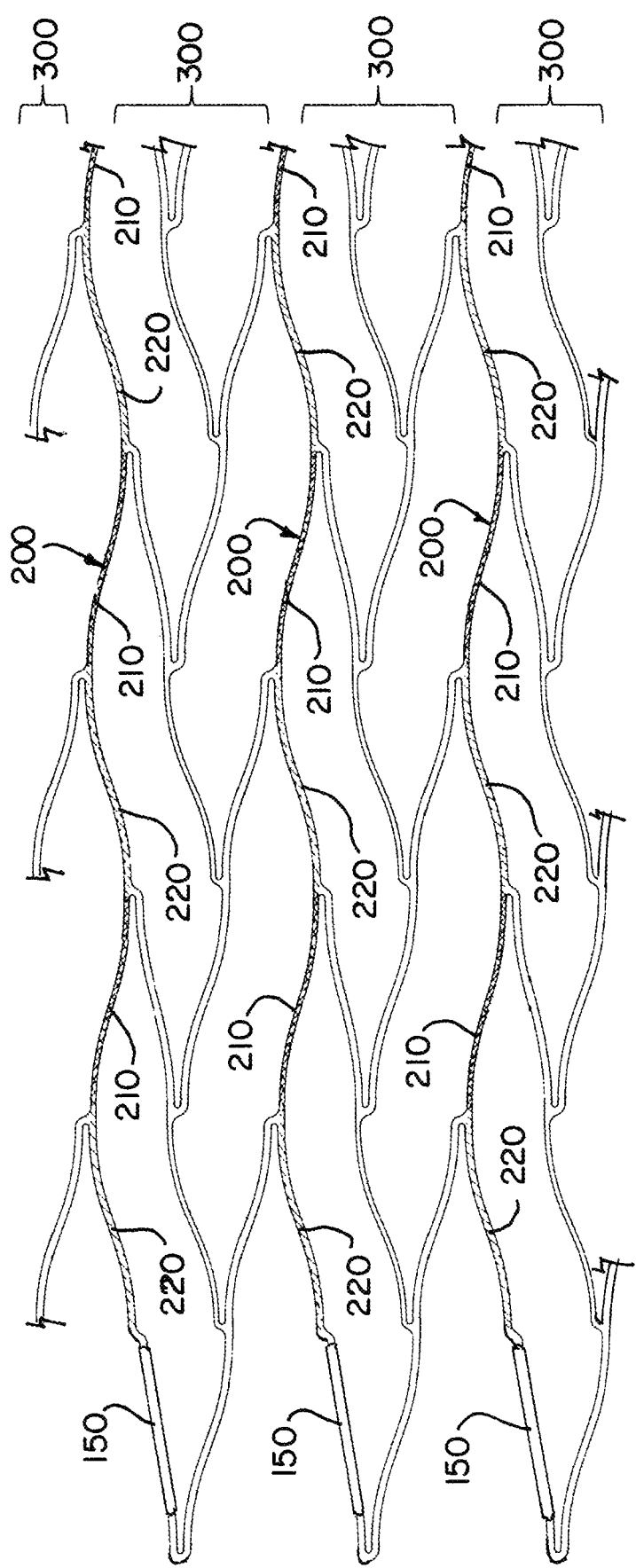
FIGS. 1C and 1D illustrate a strut pattern of a stent according to aspects of the present invention.
Figure 1D:
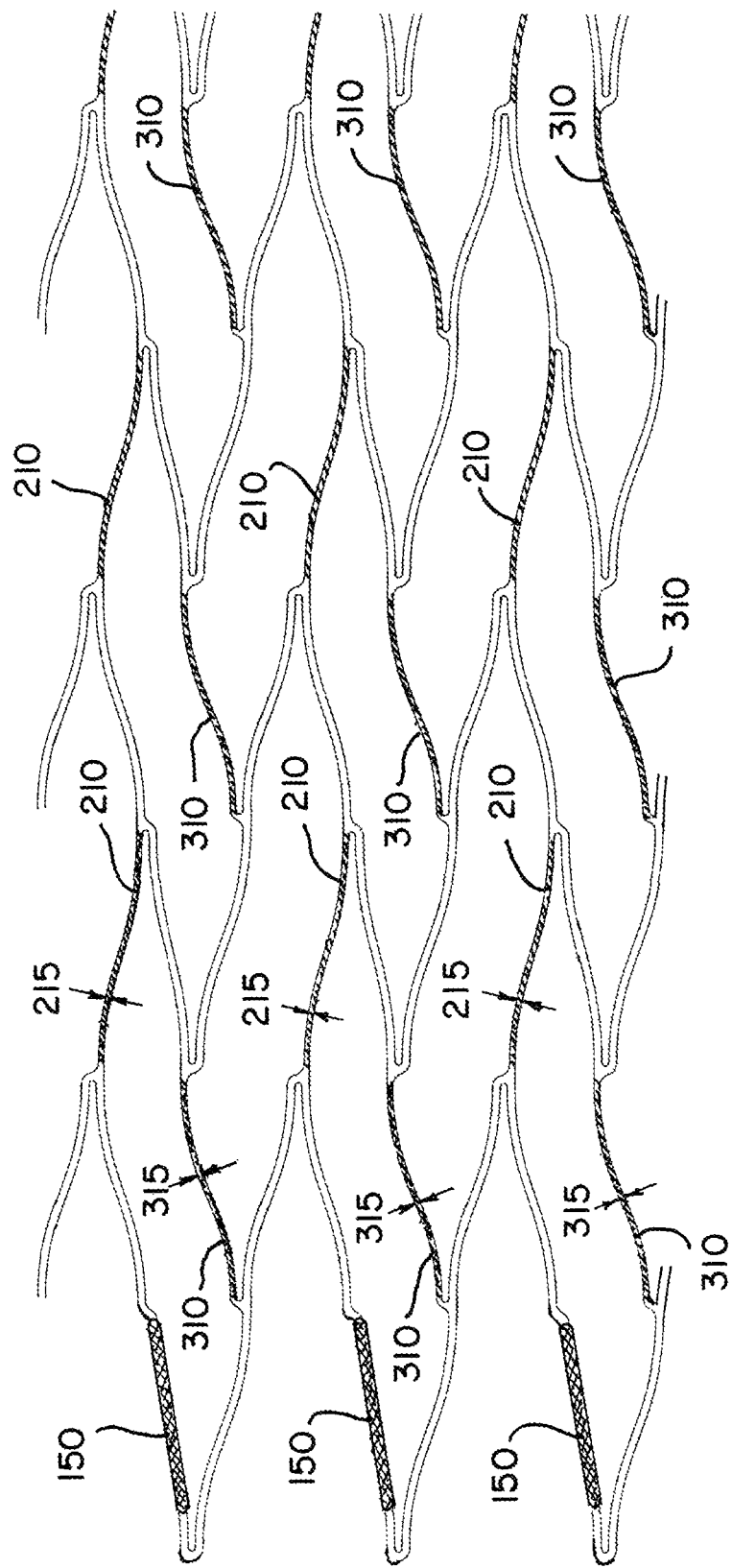

A strut pattern of an example stent 100 is illustrated in FIGS. 1A-1D. The example stent 100 is shown cut in a longitudinal direction 10 along its length 110 and laid flat. FIG. 1A illustrates an entire stent 100; FIG. 1B shows the details of a unit cell 130 as indicated in FIG. 1A; FIG. 1C illustrates the positioning of longitudinal elements 200 in relation to interconnecting members 300; and FIG. 1D illustrates the positioning of thin segments 210 of longitudinal elements 200 and thin segments 310 of interconnecting members 300.

Referring collectively to FIGS. 1A-1D, the stent 100 can be cut from an elastic tube such as nitinol, nitinol alloy, other memory shape metal, or elastic implantable tubing so that the stent 100 can have a substantially tubular structure having a first open end 112, second open end 114, a circumference 120, and a length 110. The strut pattern can be made up of longitudinal elements 200 that extend over a majority of the length 110 of the stent 100 that are connected in a circumferential direction 20 by branches of interconnecting members 300. At each end 112, 114 of the stent 100, end segments of longitudinal elements 200 can connect to end branches of interconnecting members 300 with end joining members 150. The strut pattern can include thin segments 210,310 and thick segments 220, 322, 324, 326. The pattern of the branches in the interconnecting members 300 can mimic the wave structure of the longitudinal element 200 to form a closed cell strut pattern.

The stent 100 illustrated in FIGS. 1A-1D has three longitudinal elements 200 placed circumferentially that are connected circumferentially by interconnecting members 300, where each interconnecting member 300 is shown made up of four branches 310, 322, 324, 326. As will be understood, the number of longitudinal elements 200 and the branch structure of the interconnecting members 300 can be tailored to the specific size and flexibility requirements for treatment.

Longitudinal elements 200 are shaded in FIG. 1C to differentiate longitudinal elements 200 from interconnecting members 300. Longitudinal elements 200 can be made of alternating segments or struts that vary in width or flexibility. FIG. 1C illustrates elongated elements 200 having alternating thin segments 210 and thick segments 220, for example.

Similarly, the branches of the interconnecting members 300 can vary in width or flexibility in an alternating fashion and can mimic the alternating pattern of the longitudinal elements 200. Thin segments 210 of longitudinal elements 200 having a thin width 215 and thin segments 310 of the interconnecting members 300 having a thin width 315 are shaded in FIG. 1D to differentiate the thin segments 210, 310 from the thick segments 220, 322, 324, 326.

Thinner segments having greater flexibility can contribute to the overall flexibility of the constructed stent 100 while thicker segments having greater rigidity can contribute to the overall structural strength of the constructed stent 100. The constructed stent can have improved overall implant flexibility and conformability as can be quantized by a lower flexural modulus. The resulting constructed stent can have improved flexibility in both the longitudinal and lateral directions.

Thin segments 210 or thin branches 310 can be laser cut to have a thin width 215, 315, for example about 0.00125±0.0003 inches, and thick segments 320 or thick branches 322, 324, 326 can be laser cute to have a thick width 225, 325, for example about 0.00180±0.0003 inches. Thin segments 210 or branches can allow for increased flexibility while the thicker segments or branches can maintain the structural integrity of the stent 100 and resist kinking.

Strut configurations not shown that result in an alternating pattern of flexible and rigid segments are also contemplated. For example, strut configurations including alternating patterns of shorter and longer segments, or alternating patterns of struts having thinner or thicker depths in the radial direction of the stent can result in an alternating pattern of flexible and rigid segments. Additionally, or alternatively, for stents with longitudinal elements having a wave pattern, the wavelength and/or the amplitude of the wave pattern can be modified within the stent structure to alter the flexibility/rigidity of segments of said longitudinal elements and to control the overall flexural modulus of the stent.

Although not depicted in the figures, incorporating radiopaque material is also contemplated. For example, a coating of radiopaque material such as tantalum can be deposited on surfaces of the stent by means known in the art to enhance device visibility under fluoroscopy. In some applications, it can be advantageous to deposit a thin coating of radiopaque material on stent surfaces in low strain areas.

Referring to FIGS. 1A-1B, the unit cell 130 pattern can repeat in a clockwise direction 22, a counter-clockwise direction 24, and a longitudinal direction 10. As illustrated in FIG. 1B, the unit cell 130 can have a longitudinal element 200 spanning across the width of the unit cell 130 and extending into longitudinally adjacent unit cells such that the longitudinal element 200 extends in a continuous and repeated fashion along the length 110 of the stent 100. A clockwise extending branch 326 can extend from a clockwise node 252 positioned at a peak 202 of the longitudinal element 200 wave pattern. The clockwise extending branch 326 can be part of an interconnecting member 300 that connects the longitudinal element 200 to an adjacent longitudinal element 200 in the clockwise direction 22. A counterclockwise extending branch 322 can extend from a counterclockwise node 254 positioned at a trough 204 of the longitudinal element wave pattern. The counterclockwise extending branch 322 can be part of an interconnecting member 300 that connects the longitudinal element 200 to an adjacent longitudinal element in the counterclockwise direction 24.

To illustrate how unit cells can be interconnected, FIG. 1B shows a unit cell 130, portions of a clockwise adjacent unit cell 132, a counterclockwise adjacent unit cell 134, a longitudinal adjacent unit cell 140, a cell that is clockwise adjacent the longitudinal adjacent cell 142, and a cell that is counterclockwise adjacent the longitudinal adjacent cell 144. Each of the partial unit cells illustrated represent a complete repeating pattern of the unit cell.

As shown in FIG. 1B, within the unit cell 130, the longitudinal element 200 can have a thick segment 220 having a thick width 225 and a thin segment 210 having a thin width 215. The thick segment 220 can have a substantially uniform thick width 225 spanning between a counterclockwise node 254 and a clockwise node 252. The thin segment 210 can have a substantially uniform thin width 215 spanning between the clockwise node 252 and a counterclockwise node 254 of the longitudinally adjacent cell 140. As the unit cell repeats along the length 110 of the stent 100, the longitudinal element 200 can have a repeating pattern of alternating thick segments 220 and thin segments 210.

Interconnecting members 300 can be made of branches that extend from the nodes 252,254 to connect longitudinal elements 200 in circumferentially adjacent unit cells. As shown in FIGS. 1A and 1B, an interconnecting member 300 can have four branches within a unit cell 130. As described above, the clockwise extending branch 326 can extend from a clockwise node 252 positioned at a peak 202 of the longitudinal element 200, and a counterclockwise extending branch 322 can extend from a counterclockwise node 254 positioned at a trough 204 of the longitudinal element 200. The branches can extend from the nodes of the longitudinal elements 200 at acute angles to facilitate collapsibility and flexibility of the stent 100.

One or more of the branches extending from the nodes can also extend longitudinally between unit cells. For example, the counterclockwise extending branch 322 of the unit cell 130 is shown extending from a counterclockwise node 254 positioned in the longitudinally adjacent unit cell 140. The longitudinal extension of the branch cell can facilitate collapse of the stent 100 and can mimic the wave pattern of the longitudinal element 200 to form a collapsible, flexible closed cell pattern.

The interconnecting member 300 can have intermediate branches connecting to the clockwise extending branch 326 and the counterclockwise extending branch 322, joining a clockwise extending branch 326 from a unit cell to a counterclockwise extending branch 322 in a circumferentially adjacent unit cell. For example, a first intermediate branch 310 can extend in the counterclockwise direction 24 from a first intermediate node 352 positioned on an end of the counterclockwise extending branch 322 to a second intermediate node 354 positioned on an end of a clockwise extending branch 326 of the counterclockwise adjacent unit cell 134.

In addition to extending in the counterclockwise direction 24, the counterclockwise extending branch 322 and the first intermediate branch 310 can together extend longitudinally across the majority or the entirety of the unit cell 130 and can mimic the wave pattern of the longitudinal element 200 to provide continuity in the closed cell structure of the stent 100. The first intermediate branch 310 can join the clockwise extending branch 326 of the counterclockwise adjacent unit cell 134 at an acute angle to mimic the attachment of branches 322, 326 to nodes 252, 254 at the longitudinal elements 200.

A second intermediate branch 324 can extend in the counterclockwise direction 24 from the first intermediate node 352 to join a clockwise extending branch 326 of the unit cell counterclockwise adjacent the longitudinal unit cell 144. In addition to extending in the counterclockwise direction 24, the second intermediate branch 324 and the clockwise extending branch 326 of the cell counterclockwise adjacent the longitudinal adjacent cell 144 can extend longitudinally over a width about equal to a width of a unit cell, spanning longitudinally from approximately half way across the unit cell 130 to about half way across the cell counterclockwise adjacent the longitudinal adjacent cell 144, and the longitudinal extension of the two branches can mimic the wave pattern of the longitudinal element 200. The second intermediate branch 324 can join the counterclockwise extending branch 322 at the first intermediate node 352 at an acute angle to mimic the attachment of branches 322, 326 to nodes 252, 254 at the longitudinal elements 200.

Branches in the interconnecting member 300 can have varying widths. For example, the first intermediate branch 310 can have a thin width 315 that is substantially uniform between the first intermediate node 352 and the second intermediate node 354. As shown in FIG. 1B, the clockwise extending branch 326, the counterclockwise extending branch 322, and the second intermediate branch 324 can each have a substantially uniform thick width 325 such that the thin width 315 measures less than the thick width 325.

End cells 160 can include an end segment of a longitudinal element 200 and an end branch segment connected by an end joining member 150.

Figure 2:
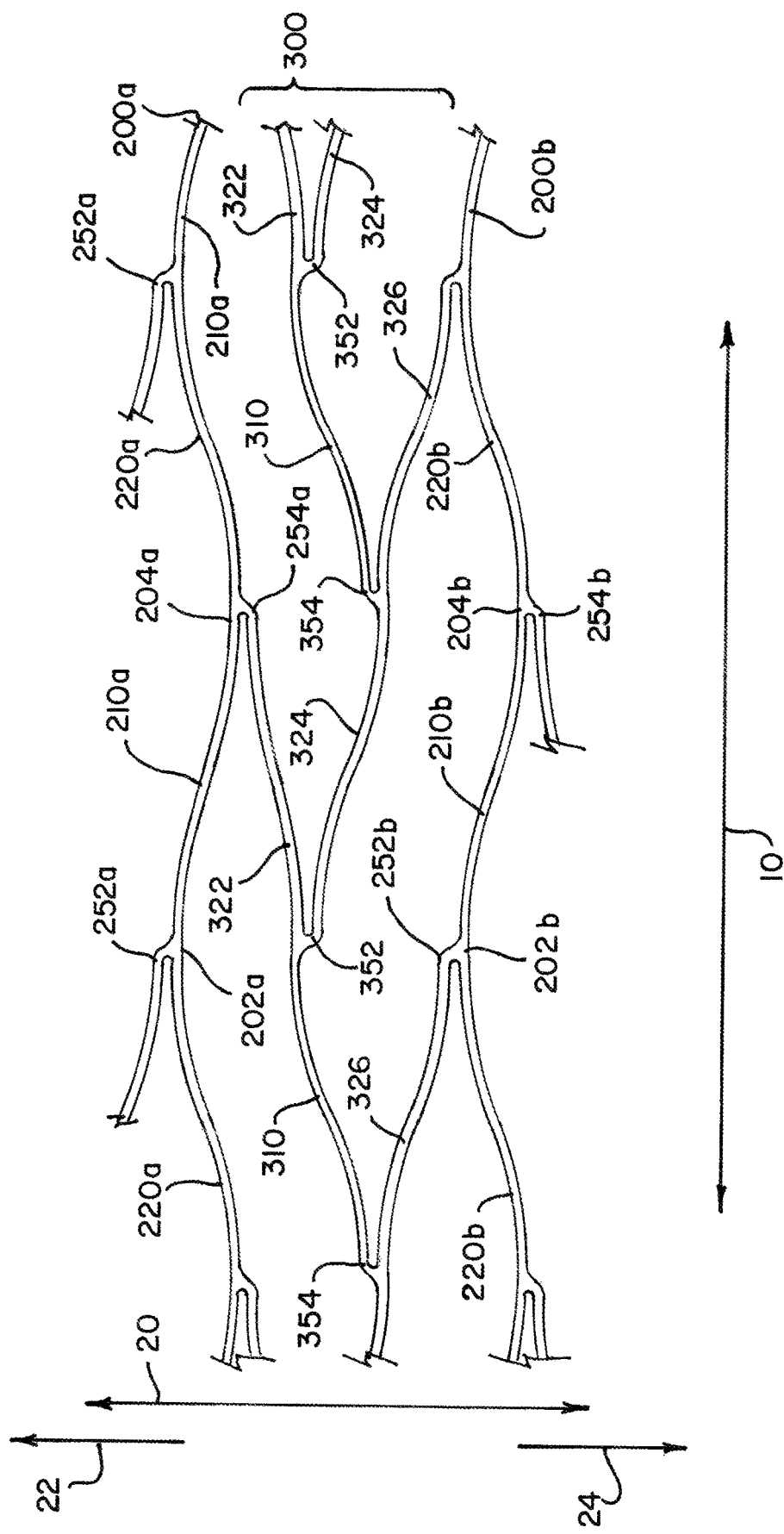
FIG. 2 illustrates a strut pattern of a stent according to aspects of the present invention.

FIG. 2 shows another visualization of an example strut pattern of the stent 100. FIG. 2 shows a first longitudinal element 200a and a second longitudinal element 200b positioned adjacent each other in the circumferential direction 20 and an interconnecting member 300 made up of branches that extend circumferentially to connect the adjacent longitudinal elements 200a, 200b. Each longitudinal element 200a, 200b has a wave pattern having peaks 202a, 202b and troughs 204a,204b with an alternating pattern of thin segments 210a,210b and thick segments 220a,220b spanning between the peaks 202a, 202b and troughs 204a, 204b. Nodes 254a positioned at troughs 204a of the first longitudinal element 200a connect to counterclockwise extending branches 322 of the interconnecting member 300, and nodes 252b positioned at peaks 202b of the second longitudinal element 200b connect to clockwise extending branches 326 of the interconnecting member 300. Nodes 252a can be positioned at peaks 202a of the first longitudinal element 200a to join with a clockwise adjacent longitudinal element (not shown), and nodes 254b can be positioned at troughs 204b of the second longitudinal element 200b to join with a counterclockwise adjacent longitudinal element (not shown).

The first and second longitudinal elements 200a, 200b can be aligned such that peaks 202a of the first longitudinal element 200a align circumferentially with peaks 202b of the second longitudinal element 200b and troughs 204a of the first longitudinal element 200a align circumferentially with troughs 204b of the second longitudinal element 200b.

First intermediate branches 310 and second intermediate branches 324 can span between first intermediate nodes 352 positioned at an end of the counterclockwise extending branches 322 and second intermediate nodes 354 positioned at an end of the clockwise extending branches 326. The first and second intermediate branches 310,324 can extend longitudinally in opposite directions between the first intermediate nodes 352 and the second intermediate nodes 354 to form a pattern that mimics the wave pattern of the longitudinal elements 200a,200b. The first and second intermediate branches 310,324 can join end-to-end at first and second intermediate nodes 352,354 to span across most of the length 110 of the stent 100. First intermediate nodes 352 can align circumferentially with peaks 202a,202b of the first longitudinal element 200a and the second longitudinal element 200b, and second intermediate nodes 354 can align circumferentially with troughs 204a,204b of the first longitudinal element 200a and the second longitudinal element 200b.

The first intermediate branches 310 can each have a thin width 315 about equal to the width 215 of the thin segments 210a,210b of the longitudinal elements 200a, 200b, and the second intermediate branches 324 can have a thick width 325 about equal to the width 225 of the thick segments 220a,220b of the longitudinal elements 200a, 200b. The thin first intermediate branches 310 can be positioned circumferentially about half way between thick segments 220a of the first longitudinal element 200a and the thick segments 220b of the second longitudinal element 200b, and the thick second intermediate branches 324 can be positioned circumferentially about half way between the thin segments 210a of the first longitudinal element 200a and the thin segments 210b of the second longitudinal element 200b. In this manner, longitudinally extending thin and thick segments can be positioned in an alternating fashion around the circumference 120 of the stent 100.

In another example not shown, longitudinal elements 200 can be used in place of intermediate branches 310,324. Referring to FIG. 2, and for the sake of visualizing such a geometry, first intermediate nodes 352 can be shaped to join first intermediate branches 310 and second intermediate branches 324 end-to-end each in the shape of a peak of a wave, and the second intermediate nodes 354 can be shaped to join the first intermediate branches 310 and second intermediate branches 324 end-to-end each in the shape of a trough of a wave. Configured thusly, the intermediate branches essentially take on the shape of the longitudinal elements 200.

Figure 3:
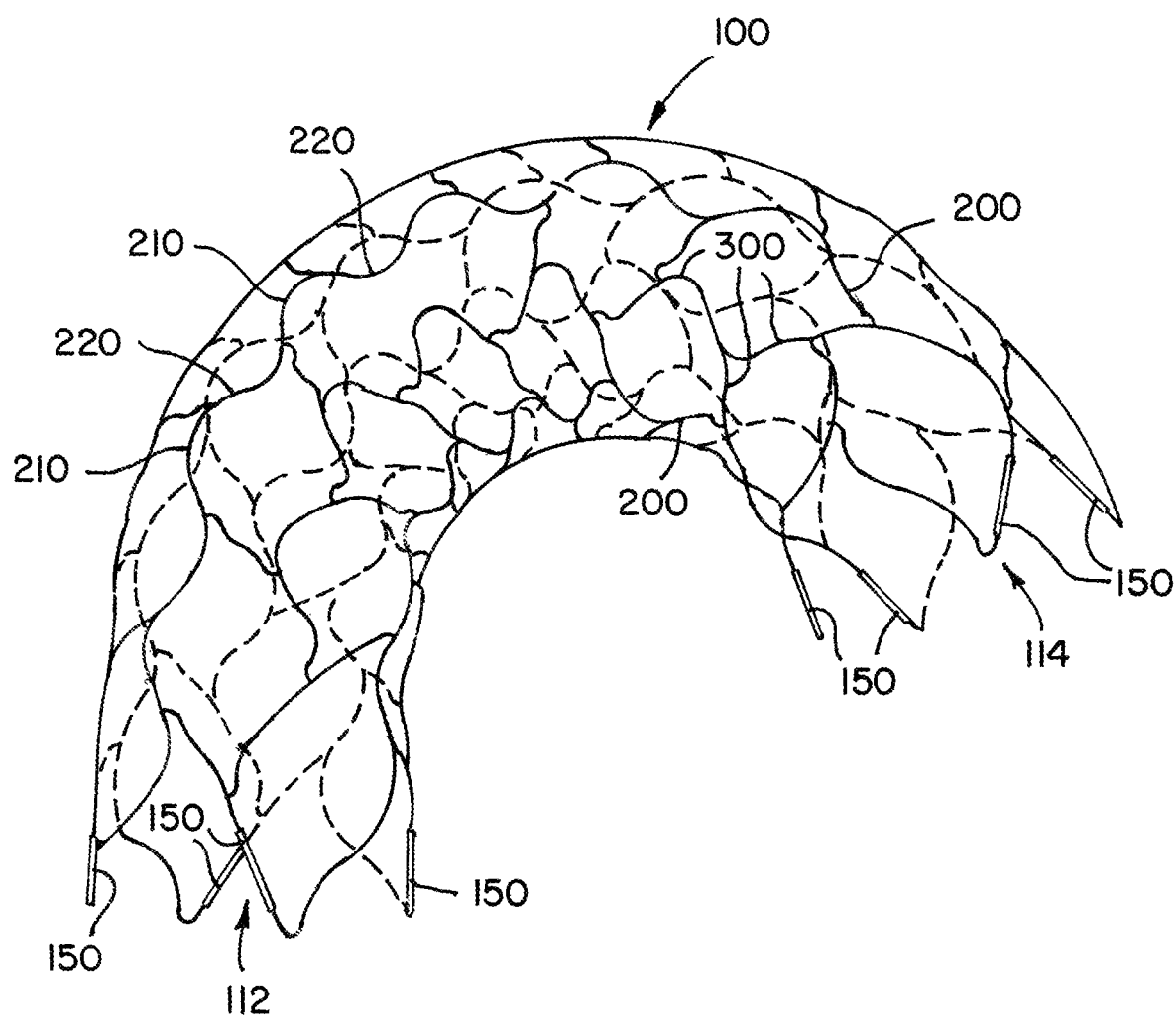
FIG. 3 illustrates a three-dimensional stent according to aspects of the present invention.

FIG. 3 is a three-dimensional illustration of an example stent 100 in a bent configuration. The stent 100 can be made up of longitudinal elements 200 spanning the length 110 of the stent 100 from a first open end 112 to a second open end 114. The longitudinal elements 200 can have alternating flexible segments 210 and rigid segments 220. The longitudinal elements 200 can be connected by interconnecting members 300 that span the length 110 of the stent 100, connecting circumferentially adjacent longitudinal elements 200. The interconnecting members 300 can be made up of branches. At each end 112, 114 of the stent 100, end joining members 150 can connect each end segment of the longitudinal elements 200 to each end branch of the interconnecting members 300.

Figure 4:
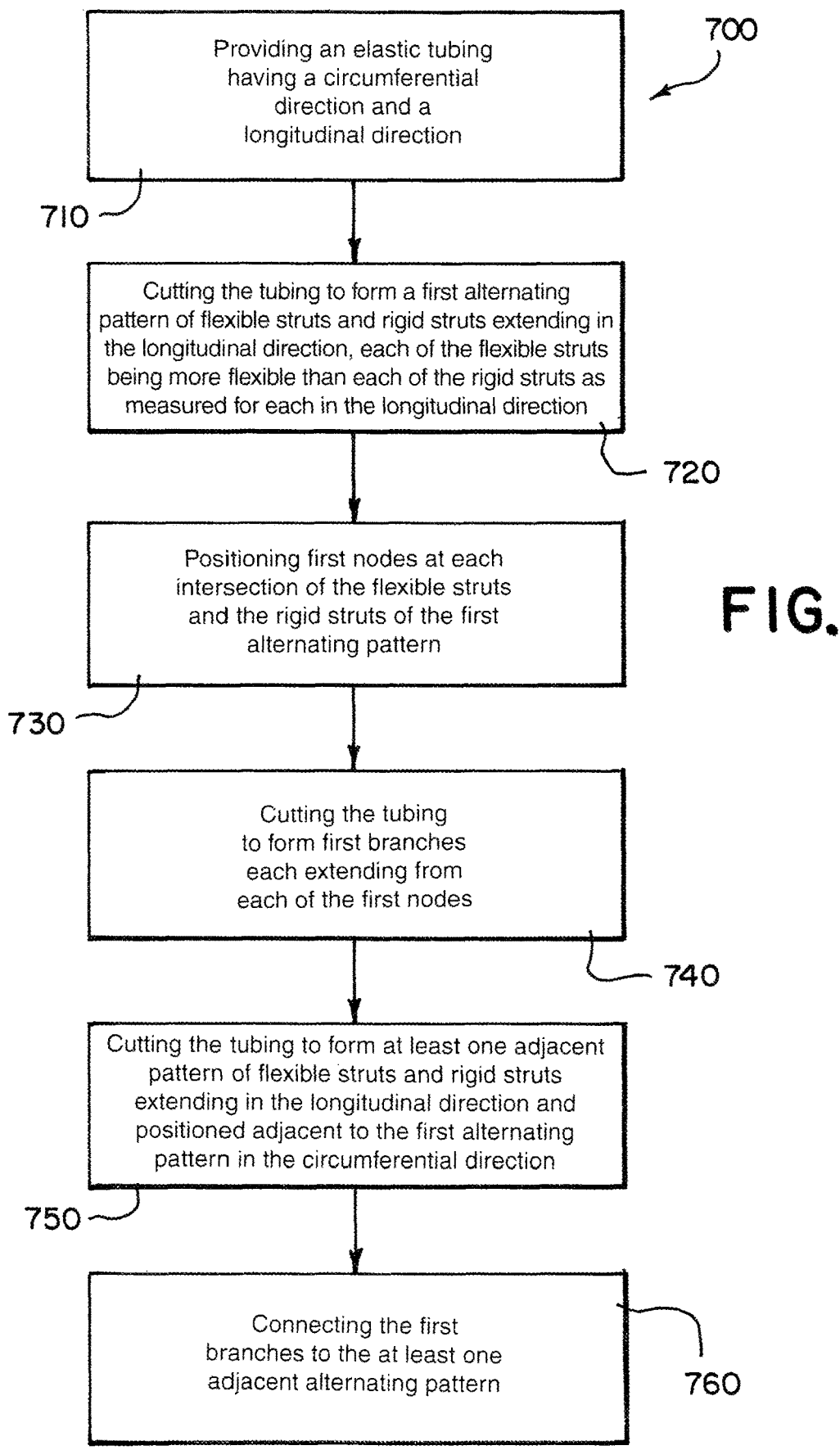
FIGS. 4 and 5 are flow diagrams including steps that can be part of a method of manufacture of a stent according to aspects of the present invention.
Figure 5:
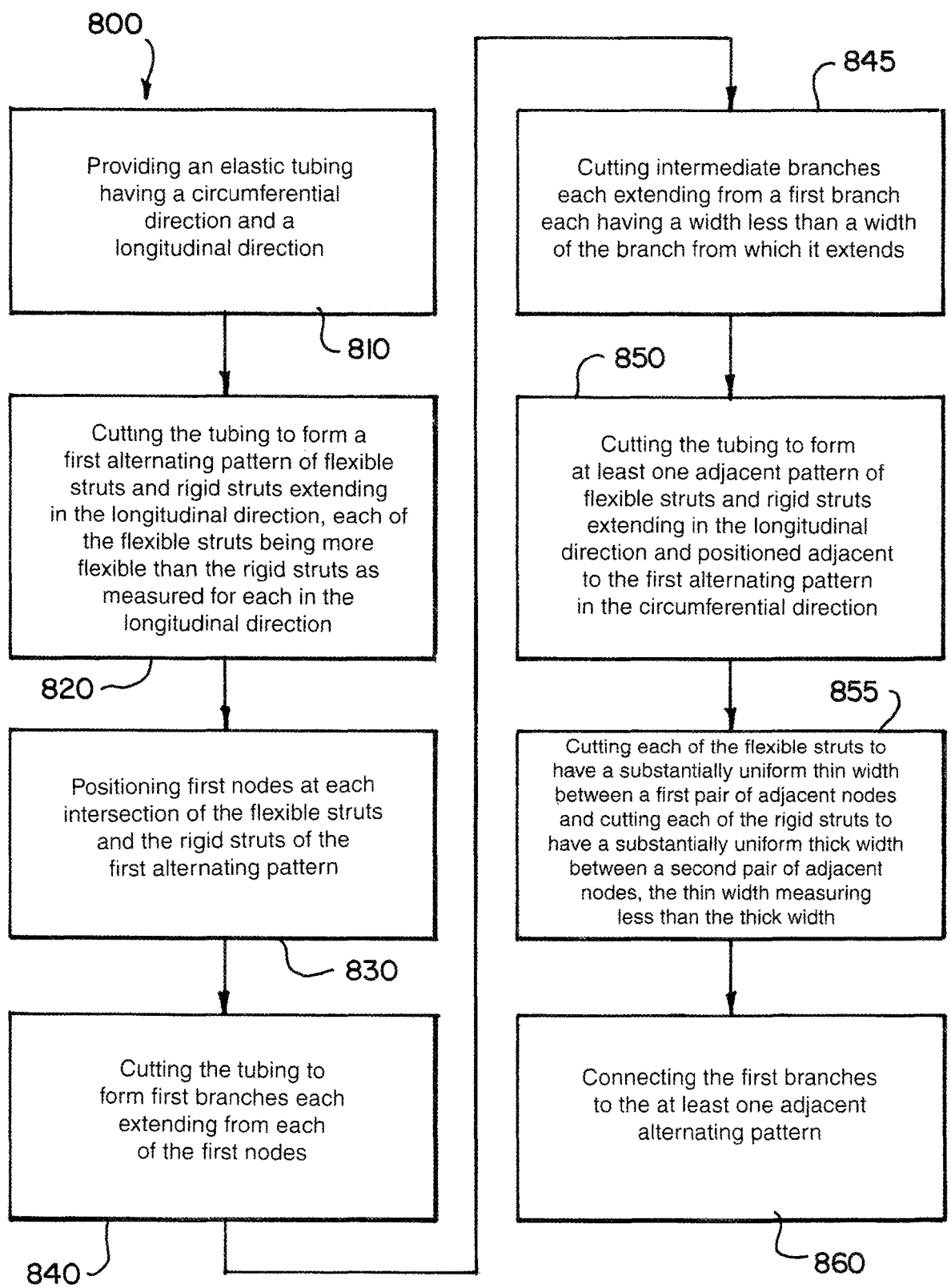

FIGS. 4 and 5 are a flow diagrams outlining example method steps that can be used in the process of manufacturing a stent. The method steps can be implemented by any of the example means described herein or by any means that would be known to one of ordinary skill in the art.

Referring to method 700 outlined in FIG. 4, in step 710 an elastic tubing having a circumferential direction and a longitudinal direction can be provided. The elastic tubing can be for example nitinol, nitinol alloy, other memory shape metal, elastic implantable tubing, or other material known in the art. In step 720, the tubing can be cut to form a first alternating pattern of flexible struts and rigid struts extending in the longitudinal direction, each of the flexible struts being more flexible than each of the rigid struts as measured for each in the longitudinal direction. In step 730 first nodes can be positioned at each intersection of the flexible struts and rigid struts of the first alternating pattern. In step 740, the tubing can be cut to form first branches such that each of the first branches extends from each of the first nodes. In step 750 the tubing can be cut to form at least one adjacent pattern of flexible struts and rigid struts extending in the longitudinal direction and positioned adjacent to the first alternating pattern in the circumferential direction. In step 760 the first branches can be connected to the at least one adjacent alternating pattern.

Referring to method 800 outlined in FIG. 5, in step 810 an elastic tubing having a circumferential direction and a longitudinal direction can be provided. The elastic tubing can be for example nitinol, nitinol alloy, other memory shape metal, elastic implantable tubing, or other material known in the art. In step 820, the tubing can be cut to form a first alternating pattern of flexible struts and rigid struts extending in the longitudinal direction, each of the flexible struts being more flexible than each of the rigid struts as measured for each in the longitudinal direction. In step 830 first nodes can be positioned at each intersection of the flexible struts and rigid struts of the first alternating pattern. In step 840, the tubing can be cut to form first branches such that each of the first branches extends from each of the first nodes. In step 845, intermediate branches can be cut such that each intermediate branch extends from a first branch, and such that each intermediate branch has a width less than the width of the first branch from which it extends. In step 850 the tubing can be cut to form at least one adjacent pattern of flexible struts and rigid struts extending in the longitudinal direction and positioned adjacent to the first alternating pattern in the circumferential direction. In step 855, each of the flexible struts can be cut to have a substantially uniform thin width between a first pair of adjacent nodes and each of the rigid struts can be cut to have a substantially uniform thick width between a second pair of adjacent nodes such that the thin width measures less than the thick width. In step 860 the first branches can be connected to the at least one adjacent alternating pattern.

The descriptions contained herein are examples of embodiments of the invention and are not intended in any way to limit the scope of the invention. As described herein, the invention contemplates many variations and modifications of the stent, including alternative shapes for the longitudinal elements, interconnecting members having more or fewer branches, interconnecting members having different geometries, additional or fewer struts, or utilizing any of numerous materials or manufacturing means for the stent, for example. These modifications would be apparent to those having ordinary skill in the art to which this invention relates and are intended to be within the scope of the claims which follow.

The invention claimed is:

1. A stent for implanting in a body lumen comprising:
a plurality of longitudinal elements extending over a majority of a length of the stent, each longitudinal element of the plurality of longitudinal elements respectively comprising a plurality of alternating thin segments and thick segments;
a plurality of nodes positioned on each longitudinal element of the plurality of longitudinal elements between each of the plurality of alternating thin segments and thick segments; and
a plurality of branches connecting circumferentially adjacent longitudinal elements of the plurality of longitudinal elements at the plurality of nodes,
wherein the plurality of thin segments each comprise a thin width that is a substantially uniform width between a first adjacent pair of the plurality of nodes, and the plurality of thick segments each comprise a thick width that is a substantially uniform width between a second adjacent pair of the plurality of nodes, the thick width measuring greater than the thin width.

2. The stent of claim 1, wherein each longitudinal element of the plurality of longitudinal elements comprises a sinusoidal shape.

3. The stent of claim 2, wherein each node of the plurality of nodes are positioned at a peak or a trough of the sinusoidal shape.

4. The stent of claim 1, wherein the plurality of branches comprises a thin branch comprising a substantially uniform width and a thick branch comprising a substantially uniform width greater than the width of the thin branch, the thin branch being joined to the thick branch circumferentially between the circumferentially adjacent longitudinal elements.

5. The stent of claim 1,
wherein the plurality of branches form a plurality of interconnecting members such that each interconnecting member of the plurality of interconnecting members comprises four branches joined at two intermediate nodes, the intermediate nodes being positioned circumferentially between pairs of adjacent longitudinal elements of the plurality of longitudinal elements and being distinct from the plurality of nodes positioned on each longitudinal element of the plurality of longitudinal elements, and
wherein a first branch of the four branches comprises a substantially uniform first width and a second branch of the four branches comprises a substantially uniform second width measuring greater than the first width.

6. The stent of claim 1, wherein the thick width measures about 0.0018 inches and the thin width measures about 0.00125 inches.

7. A stent for implanting in a body lumen, the stent comprising a substantially tubular shape and a plurality of unit cells repeating in a clockwise direction, a counterclockwise direction, and a longitudinal direction, each unit cell of the plurality of unit cells comprising:

a longitudinally extending element extending a width of the unit cell of the plurality of unit cells in the longitudinal direction and forming one period of a wave pattern comprising:
   a thick segment comprising a substantially uniform width and extending approximately half of the width of the unit cell of the plurality of unit cells, and
   a thin segment comprising a substantially uniform width that measures less than the width of the thick segment and extending approximately half of the width of the unit cell of the plurality of unit cells; a plurality of nodes positioned on each longitudinally extending element of a plurality of longitudinally extending elements between each of a plurality of alternating thin segments and thick segments;
   a clockwise extending branch extending from the longitudinally extending element circumferentially in the clockwise direction; and
   a counterclockwise extending branch extending from the longitudinally extending element circumferentially in the counterclockwise direction.

8. The stent of claim 7, the unit cell of the plurality of unit cells further comprising a first intermediate branch connecting:
   a longitudinally adjacent counterclockwise extending branch extending from a longitudinally adjacent unit cell of the plurality of unit cells and a counterclockwise adjacent clockwise extending branch extending from a counterclockwise adjacent unit cell of the plurality of unit cells.

9. The stent of claim 8, the unit cell of the plurality of unit cells further comprising a second intermediate branch connecting:
   the longitudinally adjacent counterclockwise extending branch and a diagonally adjacent clockwise extending branch extending from a unit cell of the plurality of unit cells counterclockwise adjacent the longitudinally adjacent unit cell of the plurality of unit cells.

10. The stent of claim 8, wherein:
   the clockwise extending branch comprises a substantially uniform width,
   the counterclockwise extending branch comprises a substantially uniform width measuring about equal to the width of the clockwise extending branch, and
   the first intermediate branch comprises a substantially uniform width measuring less than the width of the clockwise extending branch and the width of the counterclockwise extending branch.

11. The stent of claim 7, wherein the wave pattern is in the shape of a sinusoid.

12. The stent of claim 7, wherein the width of the thick segment measures about 0.0018 inches and the width of the thin segment measures about 0.00125 inches.

13. The stent of claim 7 further comprising a first end, a second end, a length extending in the longitudinal direction from the first end to the second end, and a plurality of end cells, each end cell comprising:
   an end segment of the longitudinally extending element;
   an end branch; and
   a joining member connecting the end segment to the end branch,
   wherein the end cells are positioned approximate the first end and the second end and repeat in the clockwise direction and the counterclockwise direction, and
   wherein the unit cells of the plurality of unit cells repeat longitudinally over a majority of the length of the stent.

14. A stent for implanting in a body lumen comprising:
   a plurality of longitudinal elements extending in a longitudinal direction over a majority of a length of the stent, each longitudinal element of the plurality of longitudinal elements respectively comprising a plurality of alternating flexible segments and rigid segments,
      wherein each of the plurality of flexible segments and each of the plurality of rigid segments provide structural support for the stent, and
      wherein the plurality of flexible segments each comprise greater flexibility in the longitudinal direction or a circumferential direction than each of the plurality of rigid segments;
   a plurality of nodes positioned on each longitudinal element of the plurality of longitudinal elements between each of the plurality of alternating flexible segments and rigid segments; and
   a plurality of branches connecting circumferentially adjacent longitudinal elements of the plurality of longitudinal elements at the plurality of nodes.

15. The stent of claim 14, wherein the plurality of flexible segments comprise a thin width, the plurality of rigid segments comprise a thick width, and the thick width is greater than the thin width.

16. The stent of claim 14, wherein the plurality of branches comprises a flexible branch and a rigid branch, the flexible branch comprising a greater flexibility in the longitudinal direction or the circumferential direction than the rigid branch.

17. The stent of claim 14, wherein
   each longitudinal element of the plurality of longitudinal elements comprises a wave shape comprising a plurality of peaks and a plurality of troughs, and
   a respective branch of the plurality of branches extends from each peak of the plurality of peaks and from each trough of the plurality of troughs respectively.

* * * * *